US00PP29659P3

(12) United States Plant Patent
Jacobs

(10) Patent No.: US PP29,659 P3
(45) Date of Patent: Sep. 11, 2018

(54) ***ALSTROEMERIA* PLANT NAMED 'ZAPRILISA'**

(50) Latin Name: *Alstroemeria hybrida*
Varietal Denomination: Zaprilisa

(71) Applicant: Henricus Cornelius Maria Jacobs, Bleiswijk (NL)

(72) Inventor: Henricus Cornelius Maria Jacobs, Bleiswijk (NL)

(73) Assignee: Van Zanten Plants B.V., Rijsenhout (NL)

( * ) Notice: Subject to any disclaimer, the term of this patent is extended or adjusted under 35 U.S.C. 154(b) by 20 days.

(21) Appl. No.: 15/530,424

(22) Filed: Jan. 12, 2017

(65) Prior Publication Data

US 2018/0199489 P1 Jul. 12, 2018

(51) Int. Cl.
*A01H 5/02* (2018.01)

(52) U.S. Cl.
USPC ..... Plt./309

(58) Field of Classification Search
USPC ..... Plt./309
See application file for complete search history.

*Primary Examiner* — Keith O Robinson
(74) *Attorney, Agent, or Firm* — C. A. Whealy

(57) ABSTRACT

A new and distinct cultivar of *Alstroemeria* plant named 'Zaprilisa', characterized by its compact, upright to outwardly spreading and uniformly mounded plant habit; vigorous growth habit; rapid growth rate; numerous bright yellow-colored flowers with red purple-colored stripes on the inner perianth segments; and excellent container and garden performance.

2 Drawing Sheets

Botanical designation: *Alstroemeria hybrida.*
Cultivar denomination: 'ZAPRILISA'.

BACKGROUND OF THE INVENTION

The present invention relates to a new and distinct cultivar of *Alstroemeria* plant, botanically known as *Alstroemeria hybrida*, commercially used as a potted and garden-type *Alstroemeria* plant and hereinafter referred to by the name 'Zaprilisa'.

The new *Alstroemeria* plant is a product of a planned breeding program conducted by the Inventor in Rijsenhout, The Netherlands. The objective of the breeding program is to create new potted *Alstroemeria* plants with uniform plant habit, freely flowering habit, attractive leaf and flower coloration and good garden performance.

The new *Alstroemeria* plant originated from a cross-pollination made by the Inventor in Rijsenhout, The Netherlands in June, 2011 of a proprietary *Alstroemeria hybrida* selection identified as code number 15780-1, not patented, as the female, or seed, parent with a proprietary *Alstroemeria hybrida* selection identified as code number 12484-1, not patented, as the male, or pollen, parent. The new *Alstroemeria* plant was discovered and selected by the Inventor as a single flowering plant from within the progeny of the stated cross-pollination in a controlled greenhouse environment in Rijsenhout, The Netherlands in May, 2012.

Asexual reproduction of the new *Alstroemeria* plant by rhizome divisions in a controlled greenhouse environment in Rijsenhout, The Netherlands since June, 2012 has shown that the unique features of this new *Alstroemeria* plant are stable and reproduced true to type in successive generations.

SUMMARY OF THE INVENTION

Plants of the new *Alstroemeria* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Zaprilisa'. These characteristics in combination distinguish 'Zaprilisa' as a new and distinct potted *Alstroemeria* plant:

1. Compact, upright to outwardly spreading and uniformly mounded plant habit.
2. Vigorous growth habit and rapid growth rate.
3. Numerous bright yellow-colored flowers with red purple-colored stripes on the inner perianth segments.
4. Excellent container and garden performance.

Plants of the new *Alstroemeria* differ primarily from plants of the female parent selection in flower size as plants of the female parent selection have larger flowers.

Plants of the new *Alstroemeria* differ primarily from plants of the male parent selection in flower bud color as plants of the male parent selection have dark orange-colored flower buds.

Plants of the new *Alstroemeria* can be compared to plants of *Alstroemeria hybrida* 'Zapriari', disclosed in U.S. Plant Pat. No. 21,806. In side-by-side comparisons, plants of the new *Alstroemeria* differ primarily from plants of 'Zapriari' in the following characteristics:

1. Plants of the new *Alstroemeria* flower about 10 days earlier than plants of 'Zapriari'.
2. Plants of the new *Alstroemeria* are more outwardly spreading than and not as upright as plants of 'Zapriari'.
3. Plants of the new *Alstroemeria* and 'Zapriari' differ slightly in flower color as flowers of 'Zapriari' are more yellow orange in color.

BRIEF DESCRIPTION OF THE PHOTOGRAPHS

The accompanying colored photographs illustrate the overall appearance of the new *Alstroemeria* plant showing the colors as true as it is reasonably possible to obtain in colored reproductions of this type. Colors in the photographs may differ slightly from the color values cited in the detailed botanical description which accurately describe the colors of the new *Alstroemeria* plant.

The photograph on the first sheet is a side perspective view of a typical flowering plant of 'Zaprilisa' grown in a container.

The photograph on the second sheet is a close-up view of a typical flowering plant of 'Zaprilisa'.

DETAILED BOTANICAL DESCRIPTION

The aforementioned photographs and following observations and measurements describe plants of the new *Alstroemeria* grown during the late winter and early spring in 14-cm containers in a glass-covered greenhouse in Rijsenhout, The Netherlands. During the production of the plants, day temperatures ranged from 15° C. to 25° C., night temperatures ranged from 10° C. to 15° C., soil temperature averaged 14° C. and minimum light levels were 5,000 lux. Plants were three months old when the photographs and the description were taken. In the following description, color references are made to The Royal Horticultural Society Colour Chart, 2007 Edition, except where general terms of ordinary dictionary significance are used.

Botanical classification: *Alstroemeria hybrida* 'Zaprilisa'.

Parentage:

*Female, or seed, parent*.—Proprietary *Alstroemeria hybrida* selection identified as code number 15780-1, not patented.

*Male or pollen parent*.—Proprietary *Alstroemeria hybrida* selection identified as code number 12484-1, not patented.

Propagation:

*Type*.—In vitro rhizogenesis.

*Time to produce a rooted young plant, summer*.—About 40 days.

*Time to produce a rooted young plant, winter*.—About 60 days.

*Root description*.—Fibrous, fleshy, thick; close to 155D in color.

*Rooting habit*.—Freely branching; medium density.

*Rhizomes*.—Shape: Elongate; rounded. Length: About 10 cm to 30 cm. Diameter: About 3 mm to 10 mm. Texture: Smooth. Color: Close to 155D.

Overall plant description:

*Plant and growth habit*.—Compact, upright to outwardly spreading and uniformly mounding plant habit; freely branching habit with numerous lateral branches, dense and bushy appearance; vigorous growth habit; rapid growth rate.

*Plant height*.—About 20 cm.

*Plant diameter* (*spread*).—About 25 cm.

Lateral branch description:

*Aspect*.—Mostly upright.

*Length*.—About 19 cm.

*Diameter*.—About 3 mm.

*Internode length*.—About 8 mm to 10 mm.

*Strength*.—Strong.

*Texture*.—Smooth, glabrous.

*Color*.—Close to 147D.

Leaf description:

*Appearance*.—Simple, asymmetrical; sessile.

*Length*.—About 7 cm to 10 cm.

*Width*.—About 2 cm to 2.5 cm.

*Shape*.—Lanceolate.

*Apex*.—Acute.

*Base*.—Cuneate.

*Margin*.—Entire.

*Texture, upper and lower surfaces*.—Smooth, glabrous; slightly glossy.

*Venation pattern*.—Parallel.

*Color*.—Developing and fully expanded leaves, upper surface: Close to N137A; venation, close to 145A. Developing and fully expanded leaves, lower surface: Close to 137B; venation, close to 145B.

Flower description:

*Flower type and habit*.—Single cup-shaped flowers arranged in compound umbels; flowers face mostly outwardly; perianth segments separate; freely flowering habit with about ten flowers developing per inflorescence.

*Natural flowering season*.—Flowering continuous during the spring in The Netherlands; early flowering habit, plants begin flowering about 70 to 80 days after planting.

*Fragrance*.—None detected.

*Flower longevity on the plant*.—About four weeks; flowers not persistent.

*Flower buds*.—Length: About 3.5 cm. Diameter: About 1.2 cm. Shape: Roughly ovoid. Color: Close to 142B.

*Umbel height*.—About 13 cm.

*Umbel diameter*.—About 14 cm.

*Flower diameter*.—About 4.5 cm.

*Flower depth*.—About 5.5 cm.

*Perianth*.—Arrangement: Six arranged in two whorls, each whorl with two lateral and one median segments. Inner perianth, lateral segments: Length: About 5 cm. Width: About 1.8 cm. Shape: Oblanceolate. Apex: Wishbone-shaped. Base: Attenuate. Margin: Entire. Texture, upper and lower surfaces: Smooth, glabrous. Color, when opening and fully opened, upper surface: Close to 14B; stripes, close to 61A; color does not change with development. Color, when opening and fully opened, lower surface: Close to 14C; color does not change with development. Inner perianth, median segment: Length: About 5 cm. Width: About 2.2 cm. Shape: Oblanceolate. Apex: Wishbone-shaped. Base: Attenuate. Margin: Entire. Texture, upper and lower surfaces: Smooth, glabrous. Color, when opening and fully opened, upper surface: Close to 14B; color does not change with development. Color, when opening and fully opened, lower surface: Close to 14C; color does not change with development. Outer perianth, lateral segments: Length: About 4.6 cm. Width: About 3.1 cm. Shape: Obovate. Apex: Emarginate with an embedded point. Base: Attenuate. Margin: Shallowly serrate. Texture, upper and lower surfaces: Smooth, glabrous. Color, when opening and fully opened, upper surface: Close to 8A; apex and central veins, close to 139B; color does not change with development. Color, when opening and fully opened, lower surface: Close to 8B; apex and central veins, close to 139B; color does not change with development. Outer perianth, median segment: Length: About 4.6 cm. Width: About 3 cm. Shape: Obovate. Apex: Emarginate with an embedded point.

Base: Attenuate. Margin: Shallowly serrate. Texture, upper and lower surfaces: Smooth, glabrous. Color, when opening and fully opened, upper surface: Close to 8A; apex and central veins, close to 139B; color does not change with development. Color, when opening and fully opened, lower surface: Close to 8B; apex and central veins, close to 139B; color does not change with development.

*Pedicels*.—Length: About 0.3 cm to 2 cm. Diameter: About 1 mm to 1.5 mm. Strength: Strong. Angle: About 30° from vertical. Texture: Smooth, glabrous. Color: Close to 143D.

*Reproductive organs*.—Stamens: Quantity per flower: Typically six. Anther shape: Elliptic. Anther length: About 2 mm. Anther color: Close to 170B. Pollen amount: Abundant. Pollen color: Close to 162D. Pistils: Quantity per flower: One. Style length: About 3 cm. Style color: Close to 170B. Stigma shape: Three-parted. Stigma color: Close to 170D. Ovary color: Close to 146D.

*Fruits and seeds*.—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have excellent garden performance and to tolerate wind, rain and temperatures from about −5° C. to about 40° C.

It is claimed:

1. A new and distinct *Alstroemeria* plant named 'Zaprilisa' as illustrated and described.

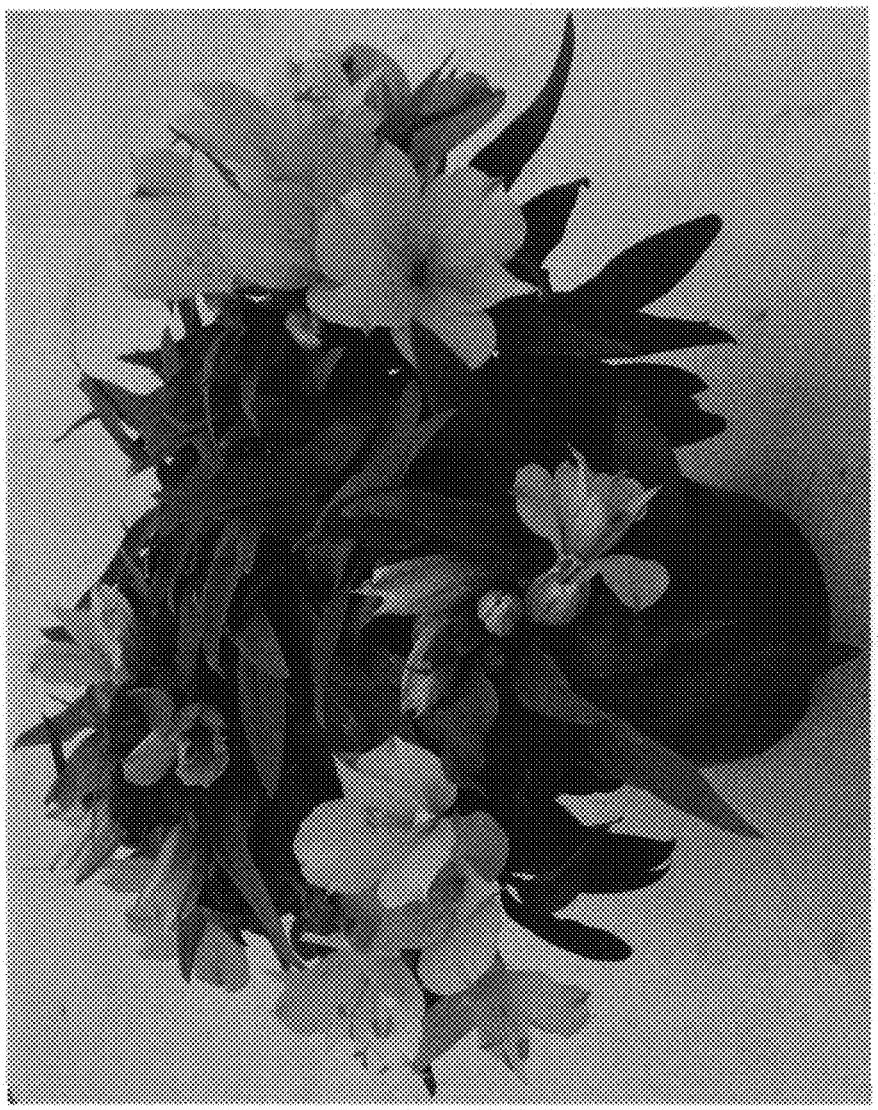

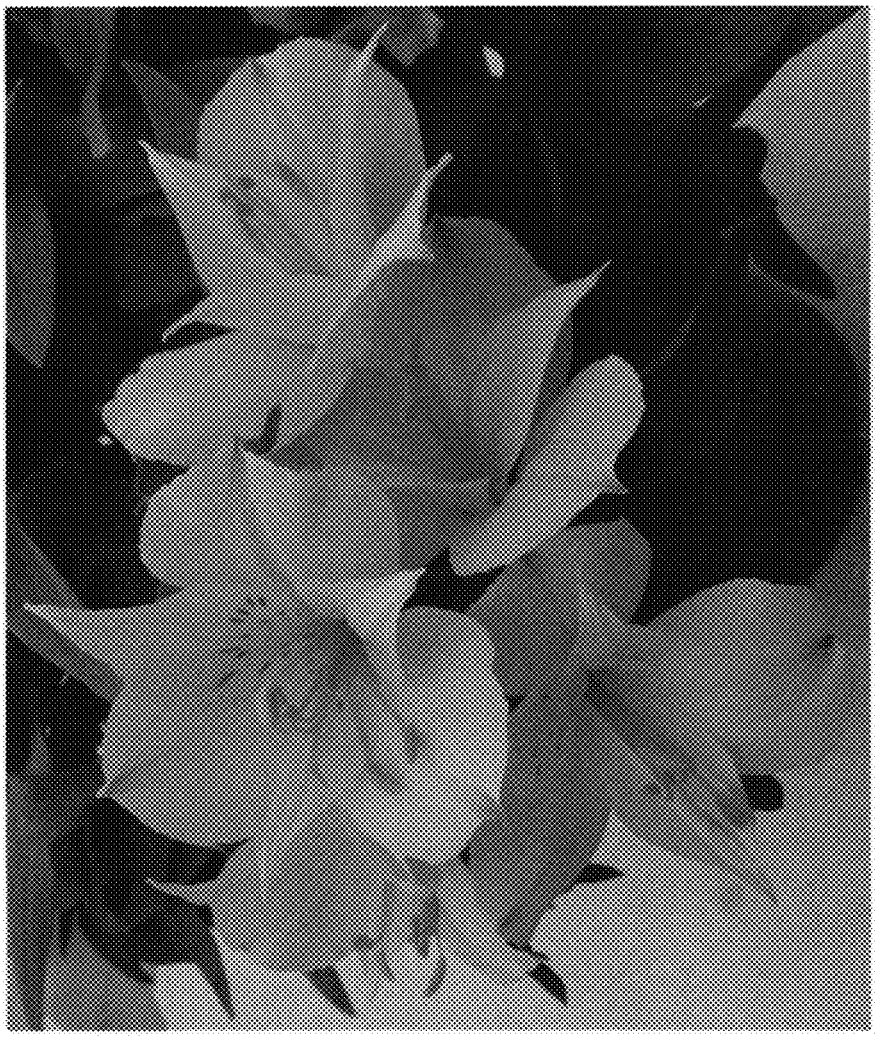

* * * * *